US012653968B2

(12) United States Patent
Rosinko

(10) Patent No.: US 12,653,968 B2
(45) Date of Patent: *Jun. 16, 2026

(54) SYSTEM AND METHOD FOR INFUSION SET DISLODGEMENT DETECTION

(71) Applicant: Tandem Diabetes Care, Inc., San Diego, CA (US)

(72) Inventor: Michael Rosinko, Anaheim, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 1077 days.

This patent is subject to a terminal disclaimer.

(21) Appl. No.: 17/738,500

(22) Filed: May 6, 2022

(65) Prior Publication Data

US 2022/0257876 A1      Aug. 18, 2022

Related U.S. Application Data

(63) Continuation of application No. 16/781,051, filed on Feb. 4, 2020, now Pat. No. 11,324,898, which is a continuation of application No. 15/871,665, filed on Jan. 15, 2018, now Pat. No. 10,549,051, which is a continuation of application No. 13/923,556, filed on Jun. 21, 2013, now Pat. No. 9,867,953.

(51) Int. Cl.
*A61M 5/50* (2006.01)
*A61M 5/168* (2006.01)

(52) U.S. Cl.
CPC ...... *A61M 5/5086* (2013.01); *A61M 5/16836* (2013.01); *A61M 2205/13* (2013.01)

(58) Field of Classification Search
CPC .......... A61M 2205/13; A61M 5/16836; A61M 5/5086; A61M 5/50; A61M 5/14; A61M 5/168; A61M 5/16831; A61M 5/14244; A61M 5/14248; A61M 2005/1588
See application file for complete search history.

(56) References Cited

U.S. PATENT DOCUMENTS

| | | | |
|---|---|---|---|
| 5,299,571 | A | 4/1994 | Mastrototaro |
| 5,741,211 | A | 4/1998 | Renirie et al. |
| 5,919,216 | A | 7/1999 | Houben et al. |
| 5,951,521 | A | 9/1999 | Mastrototaro et al. |
| 6,669,663 | B1 | 12/2003 | Thompson |

(Continued)

FOREIGN PATENT DOCUMENTS

| | | |
|---|---|---|
| CA | 2690742 C | 5/2018 |
| EP | 2624745 A2 | 8/2013 |

(Continued)

OTHER PUBLICATIONS

Application and file history for U.S. Appl. No. 13/923,556, filed Jun. 21, 2013, Inventors Rosinko.

(Continued)

*Primary Examiner* — Jason E Flick
(74) *Attorney, Agent, or Firm* — Merchant & Gould P.C.

(57) ABSTRACT

A portable insulin pump can utilize readings from a sensor incorporated into an infusion set used with the pump to deliver insulin to a patient to determine if the infusion set is or is likely to become dislodged from the patient. Readings from the sensor that are inconsistent with expected readings or a range of expected readings can indicate that the infusion set has become dislodged from the patient.

20 Claims, 9 Drawing Sheets

(56) References Cited

U.S. PATENT DOCUMENTS

| | | | |
|---|---|---|---|
| 6,862,466 | B2 | 3/2005 | Ackerman |
| 7,267,665 | B2 | 9/2007 | Steil et al. |
| 7,354,420 | B2 | 4/2008 | Steil et al. |
| 7,399,401 | B2 | 7/2008 | Rush |
| 7,402,153 | B2 | 7/2008 | Steil et al. |
| 7,497,827 | B2 | 3/2009 | Brister et al. |
| 7,515,060 | B2 | 4/2009 | Blomquist |
| 7,615,007 | B2 | 11/2009 | Shults et al. |
| 7,618,369 | B2 | 11/2009 | Hayter et al. |
| 7,717,903 | B2 | 5/2010 | Estes et al. |
| 7,766,829 | B2 | 8/2010 | Sloan et al. |
| 7,768,386 | B2 | 8/2010 | Hayter et al. |
| 7,785,313 | B2 | 8/2010 | Mastrototaro |
| 7,806,886 | B2 | 10/2010 | Kanderian, Jr. et al. |
| 7,882,611 | B2 | 2/2011 | Shah et al. |
| 7,935,074 | B2 | 5/2011 | Plahey et al. |
| 7,938,797 | B2 | 5/2011 | Estes |
| 7,942,844 | B2 | 5/2011 | Moberg et al. |
| 7,946,985 | B2 | 5/2011 | Mastrototaro et al. |
| 7,959,598 | B2 | 6/2011 | Estes |
| 7,981,034 | B2 | 7/2011 | Jenewine et al. |
| 7,996,158 | B2 | 8/2011 | Hayter et al. |
| 8,095,197 | B2 | 1/2012 | Santini, Jr. et al. |
| 8,109,921 | B2 | 2/2012 | Estes et al. |
| 8,119,593 | B2 | 2/2012 | Richardson et al. |
| 8,121,857 | B2 | 2/2012 | Galasso et al. |
| 8,140,312 | B2 | 3/2012 | Hayter et al. |
| 8,206,296 | B2 | 6/2012 | Jennewine |
| 8,221,385 | B2 | 7/2012 | Estes |
| 8,226,558 | B2 | 7/2012 | Say et al. |
| 8,277,435 | B2 | 10/2012 | Estes |
| 8,287,454 | B2 | 10/2012 | Wolpert et al. |
| 8,287,487 | B2 | 10/2012 | Estes |
| 8,287,495 | B2 | 10/2012 | Michaud et al. |
| 8,298,184 | B2 | 10/2012 | Diperna et al. |
| 8,337,486 | B2 | 12/2012 | Yodfat |
| 8,343,092 | B2 | 1/2013 | Rush et al. |
| 8,344,847 | B2 | 1/2013 | Moberg et al. |
| 8,348,885 | B2 | 1/2013 | Moberg et al. |
| 8,348,886 | B2 | 1/2013 | Kanderian, Jr. et al. |
| 8,348,923 | B2 | 1/2013 | Kanderian, Jr. et al. |
| 8,353,881 | B2 * | 1/2013 | Jennewine ........ A61M 5/14244 |
| | | | 604/523 |
| 8,377,031 | B2 | 2/2013 | Hayter et al. |
| 8,454,576 | B2 | 6/2013 | Mastrototaro et al. |
| 8,573,027 | B2 | 11/2013 | Rosinko et al. |
| 8,579,853 | B2 | 11/2013 | Reggiardo et al. |
| 8,595,607 | B2 | 11/2013 | Nekoomaram |
| 8,650,937 | B2 | 2/2014 | Brown |
| 8,726,266 | B2 | 5/2014 | Kiaie |
| 8,986,253 | B2 | 3/2015 | Diperna |
| 9,089,305 | B2 | 7/2015 | Hovorka |
| 9,114,210 | B2 | 8/2015 | Estes |
| 9,259,175 | B2 | 2/2016 | Stafford |
| 9,277,010 | B2 | 3/2016 | Venkatesh et al. |
| 9,326,709 | B2 | 5/2016 | Budiman |
| 9,381,297 | B2 | 7/2016 | Brown et al. |
| 9,486,171 | B2 | 11/2016 | Saint |
| 9,555,186 | B2 | 1/2017 | Kruse |
| 9,669,160 | B2 | 6/2017 | Harris |
| 9,833,177 | B2 | 12/2017 | Blomquist |
| 9,867,937 | B2 | 1/2018 | Saint et al. |
| 9,867,953 | B2 | 1/2018 | Rosinko |
| 9,968,306 | B2 | 5/2018 | Cole |
| 10,016,561 | B2 | 7/2018 | Saint et al. |
| 10,052,049 | B2 | 8/2018 | Blomquist et al. |
| 10,213,547 | B2 | 2/2019 | Rosinko |
| 10,357,606 | B2 | 7/2019 | Rosinko et al. |
| 10,357,607 | B2 | 7/2019 | Blomquist et al. |
| 10,549,051 | B2 | 2/2020 | Rosinko |
| 10,569,016 | B2 | 2/2020 | Rosinko |
| 10,864,322 | B2 | 12/2020 | Saint et al. |
| 2002/0198483 | A1 | 12/2002 | Wariar et al. |
| 2003/0060765 | A1 | 3/2003 | Campbell et al. |
| 2005/0038325 | A1 | 2/2005 | Moll |
| 2005/0137530 | A1 | 6/2005 | Campbell et al. |
| 2006/0130591 | A1 | 6/2006 | Perkins |
| 2006/0195064 | A1 | 8/2006 | Plahey et al. |
| 2006/0224141 | A1 | 10/2006 | Rush et al. |
| 2007/0033074 | A1 | 2/2007 | Nitzan et al. |
| 2007/0106135 | A1 | 5/2007 | Sloan |
| 2007/0213657 | A1 | 9/2007 | Jennewine |
| 2007/0251835 | A1 | 11/2007 | Mehta et al. |
| 2007/0253021 | A1 | 11/2007 | Mehta et al. |
| 2007/0253380 | A1 | 11/2007 | Jollota et al. |
| 2007/0254593 | A1 | 11/2007 | Jollota et al. |
| 2007/0255116 | A1 | 11/2007 | Mehta et al. |
| 2007/0255125 | A1 | 11/2007 | Moberg et al. |
| 2007/0255126 | A1 | 11/2007 | Moberg et al. |
| 2007/0255348 | A1 | 11/2007 | Holtzclaw |
| 2007/0258395 | A1 | 11/2007 | Jollota et al. |
| 2008/0004601 | A1 | 1/2008 | Jennewine et al. |
| 2008/0065006 | A1 | 3/2008 | Roger et al. |
| 2008/0071580 | A1 | 3/2008 | Marcus et al. |
| 2008/0097246 | A1 | 4/2008 | Stafford |
| 2008/0103447 | A1 | 5/2008 | Reggiardo |
| 2008/0119707 | A1 | 5/2008 | Stafford |
| 2008/0171967 | A1 | 7/2008 | Blomquist et al. |
| 2008/0172026 | A1 | 7/2008 | Blomquist |
| 2008/0172027 | A1 | 7/2008 | Blomquist |
| 2008/0172028 | A1 | 7/2008 | Blomquist |
| 2008/0172029 | A1 | 7/2008 | Blomquist |
| 2008/0172030 | A1 | 7/2008 | Blomquist |
| 2008/0172031 | A1 | 7/2008 | Blomquist |
| 2008/0195060 | A1 | 8/2008 | Roger et al. |
| 2008/0201169 | A1 | 8/2008 | Galasso |
| 2008/0228056 | A1 | 9/2008 | Blomquist et al. |
| 2008/0269714 | A1 | 10/2008 | Mastrototaro et al. |
| 2008/0269723 | A1 | 10/2008 | Mastrototaro et al. |
| 2008/0300572 | A1 | 12/2008 | Rankers et al. |
| 2009/0005724 | A1 | 1/2009 | Regittnig et al. |
| 2009/0036753 | A1 | 2/2009 | King |
| 2009/0054750 | A1 | 2/2009 | Jennewine |
| 2009/0062767 | A1 | 3/2009 | Van et al. |
| 2009/0069745 | A1 | 3/2009 | Estes et al. |
| 2009/0082647 | A1 | 3/2009 | Busby |
| 2009/0082653 | A1 | 3/2009 | Rohde |
| 2009/0088731 | A1 | 4/2009 | Campbell et al. |
| 2009/0105636 | A1 | 4/2009 | Hayter et al. |
| 2009/0112626 | A1 | 4/2009 | Talbot et al. |
| 2009/0113295 | A1 | 4/2009 | Halpern et al. |
| 2009/0163855 | A1 | 6/2009 | Shin et al. |
| 2009/0164239 | A1 | 6/2009 | Hayter |
| 2009/0171269 | A1 | 7/2009 | Jennewine et al. |
| 2009/0221890 | A1 | 9/2009 | Saffer et al. |
| 2009/0254037 | A1 | 10/2009 | Bryant, Jr. et al. |
| 2009/0275887 | A1 | 11/2009 | Estes |
| 2010/0010330 | A1 | 1/2010 | Rankers et al. |
| 2010/0049164 | A1 | 2/2010 | Estes |
| 2010/0057040 | A1 | 3/2010 | Hayter |
| 2010/0076412 | A1 | 3/2010 | Rush et al. |
| 2010/0094251 | A1 | 4/2010 | Estes |
| 2010/0114015 | A1 | 5/2010 | Kanderian, Jr. et al. |
| 2010/0168538 | A1 | 7/2010 | Keenan et al. |
| 2010/0174266 | A1 | 7/2010 | Estes |
| 2010/0198034 | A1 | 8/2010 | Thomas et al. |
| 2010/0222735 | A1 | 9/2010 | Plahey et al. |
| 2010/0228186 | A1 | 9/2010 | Estes et al. |
| 2010/0274108 | A1 | 10/2010 | Reggiardo et al. |
| 2010/0274218 | A1 | 10/2010 | Yodfat et al. |
| 2010/0274515 | A1 | 10/2010 | Hoss et al. |
| 2010/0274592 | A1 | 10/2010 | Nitzan et al. |
| 2010/0298685 | A1 | 11/2010 | Hayter et al. |
| 2010/0305545 | A1 | 12/2010 | Kanderian, Jr. et al. |
| 2010/0313105 | A1 | 12/2010 | Nekoomaram |
| 2010/0324382 | A1 | 12/2010 | Cantwell et al. |
| 2011/0006876 | A1 | 1/2011 | Moberg et al. |
| 2011/0009725 | A1 | 1/2011 | Hill et al. |
| 2011/0009813 | A1 | 1/2011 | Rankers |
| 2011/0021898 | A1 | 1/2011 | Wei et al. |
| 2011/0040247 | A1 | 2/2011 | Mandro et al. |
| 2011/0047499 | A1 | 2/2011 | Mandro et al. |
| 2011/0050428 | A1 | 3/2011 | Istoc |
| 2011/0071372 | A1 | 3/2011 | Sloan et al. |

(56) References Cited

U.S. PATENT DOCUMENTS

| | | | |
|---|---|---|---|
| 2011/0105873 A1 | 5/2011 | Feldman et al. | |
| 2011/0105955 A1 | 5/2011 | Yudovsky et al. | |
| 2011/0106050 A1 | 5/2011 | Yodfat et al. | |
| 2011/0144586 A1 | 6/2011 | Michaud et al. | |
| 2011/0144616 A1 | 6/2011 | Michaud et al. | |
| 2011/0152770 A1 | 6/2011 | Diperna et al. | |
| 2011/0152824 A1 | 6/2011 | Diperna et al. | |
| 2011/0166544 A1 | 7/2011 | Verhoef et al. | |
| 2011/0178462 A1 | 7/2011 | Moberg et al. | |
| 2011/0184342 A1 | 7/2011 | Pesach et al. | |
| 2011/0193704 A1* | 8/2011 | Harper | A61B 5/14532 |
| | | | 340/505 |
| 2011/0196213 A1 | 8/2011 | Thukral et al. | |
| 2011/0196289 A1 | 8/2011 | Plahey et al. | |
| 2011/0208155 A1 | 8/2011 | Palerm et al. | |
| 2011/0213225 A1 | 9/2011 | Bernstein et al. | |
| 2011/0224523 A1 | 9/2011 | Budiman | |
| 2011/0257627 A1* | 10/2011 | Hovorka | G16H 70/40 |
| | | | 604/504 |
| 2012/0029433 A1 | 2/2012 | Michaud et al. | |
| 2012/0030610 A1 | 2/2012 | Diperna et al. | |
| 2012/0053522 A1 | 3/2012 | Yodfat et al. | |
| 2012/0123230 A1 | 5/2012 | Brown et al. | |
| 2012/0245447 A1 | 9/2012 | Karan | |
| 2012/0277667 A1 | 11/2012 | Yodfat et al. | |
| 2013/0053816 A1 | 2/2013 | Diperna et al. | |
| 2013/0237955 A1 | 9/2013 | Neta et al. | |
| 2014/0005633 A1 | 1/2014 | Finan | |
| 2014/0012511 A1 | 1/2014 | Mensinger et al. | |
| 2014/0033002 A1 | 1/2014 | Nekoomaram | |
| 2014/0137641 A1 | 5/2014 | Brown | |
| 2014/0171772 A1 | 6/2014 | Blomquist | |
| 2014/0187890 A1 | 7/2014 | Mensinger | |
| 2014/0200426 A1 | 7/2014 | Taub | |
| 2014/0273042 A1 | 9/2014 | Saint | |
| 2014/0276419 A1 | 9/2014 | Rosinko et al. | |
| 2014/0276423 A1 | 9/2014 | Lecanu-Fayet | |
| 2014/0276556 A1 | 9/2014 | Saint et al. | |
| 2014/0350371 A1 | 11/2014 | Blomquist et al. | |
| 2015/0052511 A1 | 2/2015 | Kiaie | |
| 2015/0151082 A1 | 6/2015 | Gescheit | |
| 2015/0182693 A1 | 7/2015 | Rosinko | |
| 2016/0030669 A1 | 2/2016 | Harris et al. | |
| 2016/0082188 A1 | 3/2016 | Blomquist et al. | |
| 2016/0199571 A1 | 7/2016 | Rosinko et al. | |
| 2017/0000943 A1 | 1/2017 | Blomquist et al. | |
| 2017/0173261 A1 | 6/2017 | O'Connor | |
| 2017/0216524 A1 | 8/2017 | Haider | |
| 2018/0092578 A1 | 4/2018 | Blomquist | |
| 2019/0313905 A1 | 10/2019 | Mensinger | |
| 2019/0328967 A1 | 10/2019 | Blomquist et al. | |
| 2019/0350501 A1 | 11/2019 | Blomquist et al. | |
| 2019/0365997 A1 | 12/2019 | Harris | |
| 2019/0388015 A1 | 12/2019 | Blomquist | |
| 2020/0101226 A1 | 4/2020 | Rosinko et al. | |
| 2020/0114076 A1 | 4/2020 | Ulrich et al. | |
| 2020/0179603 A1 | 6/2020 | Rosinko | |
| 2020/0254174 A1 | 8/2020 | Kruse et al. | |
| 2020/0261649 A1 | 8/2020 | Michaud et al. | |
| 2020/0368430 A1 | 11/2020 | Ulrich et al. | |
| 2021/0001044 A1 | 1/2021 | Michaud et al. | |

FOREIGN PATENT DOCUMENTS

| | | |
|---|---|---|
| EP | 2438527 B1 | 5/2018 |
| EP | 3319518 A1 | 5/2018 |
| WO | 9528878 A1 | 11/1995 |
| WO | 2007149533 A1 | 12/2007 |
| WO | 2009032400 A1 | 3/2009 |
| WO | 2009035759 A1 | 3/2009 |
| WO | 2009147680 A2 | 12/2009 |
| WO | 2010033878 A2 | 3/2010 |
| WO | 2011014704 A2 | 2/2011 |
| WO | 2013184896 A1 | 12/2013 |
| WO | 2018085600 A1 | 5/2018 |

OTHER PUBLICATIONS

Application and file history for U.S. Appl. No. 15/871,665, filed Jan. 15, 2018, Inventors Rosinko.

Application and file history for U.S. Appl. No. 16/793,662, filed Feb. 18, 2020, Inventors Michaud.

International Search report and Written Opinion for Application No. PCT/US2014/018834, mailed on Jul. 1, 2014, 13 pages.

International Search Report and Written Opinion for Application No. PCT/US2014/018834, mailed on Dec. 30, 2015, 10 pages.

* cited by examiner

SYSTEM AND METHOD FOR INFUSION SET DISLODGEMENT DETECTION

RELATED APPLICATIONS

This application is a continuation of U.S. application Ser. No. 16/781,051 filed Feb. 4, 2020, which in turn is a continuation of U.S. application Ser. No. 15/871,665 filed Jan. 15, 2018, now U.S. Pat. No. 10,549,051 issued Feb. 4, 2020, which in turn is a continuation of U.S. application Ser. No. 13/923,556 filed Jun. 21, 2013, now U.S. Pat. No. 9,867,953 issued Jan. 16, 2018, which are hereby fully incorporated herein by reference.

FIELD OF THE INVENTION

The present invention is directed to pumps for the delivery of fluid, such as medicament including insulin, and, more particularly to detecting dislodgement of an infusion set that delivers medicament from the pump to a patient from the patient's skin.

BACKGROUND

There are many applications in academic, industrial, and medical fields that benefit from devices and methods that are capable of accurately and controllably delivering fluids, such as liquids and gases that have a beneficial effect when administered in known and controlled quantities. Such devices and methods can be particularly useful in the medical field where treatments for many patients include the administration of a known amount of a substance at predetermined intervals.

Insulin-injecting pumps have been developed for the administration of insulin for those suffering from both type I and type II diabetes. Some insulin injecting pumps configured as portable infusion devices can provide continuous subcutaneous insulin injection and/or infusion therapy for the treatment of diabetes. Such therapy may include the regular and/or continuous injection or infusion of insulin into the skin of a person suffering from diabetes, and offers an alternative to multiple daily injections of insulin by an insulin syringe or an insulin pen. Such pumps can be ambulatory/portable infusion pumps that are worn by the user and that may use replaceable cartridges. Examples of such pumps and various features that can be associated with such pumps include those disclosed in U.S. patent application Ser. No. 13/557,163, U.S. patent application Ser. No. 12/714,299, U.S. patent application Ser. No. 12/538,018, U.S. patent application Ser. No. 13/838,617, U.S. patent application Ser. No. 13/827,707 and U.S. Pat. No. 8,287, 495, each of which is incorporated herein by reference.

Infusions pumps such as those described above deliver medicament to patients through infusion sets that include tubing extending from the pump and a cannula with an associated needle that penetrates the patient's skin to allow infusion of the medicament through the cannula and into the patient. The cannula typically is held in place on the patient's skin with an adhesive patch. If the patch loosens from the patient's skin, the cannula can become disconnected from the patient, preventing the patient from receiving the medicament and potentially causing serious health concerns. In the case of insulin pumps, in many circumstances the flow of insulin through the cannula is relatively low, so the insulin may evaporate prior to contacting the patient's skin adjacent the insertion site such that the patient does not notice that insulin is not being received.

Therefore, there is a need for a system and a method that can automatically and reliably identify when an infusion set has become dislodged from a patient's skin.

SUMMARY OF THE INVENTION

A portable insulin pump can utilize readings from a sensor incorporated into an infusion set used with the pump to deliver insulin to a patient to determine if the infusion set is or is likely to become dislodged from the patient. Readings from the sensor that are inconsistent with expected readings or a range of expected readings can indicate that the infusion set has become dislodged from the patient.

In some embodiments, a portable infusion pump includes a user interface, a receiver and a processor functionally linked to the user interface and receiver. The receiver can be adapted to receive information obtained by a glucose sensor, such as continuous glucose sensor. The processor can analyze the information from the glucose sensor and determine from that information whether or not an infusion set connecting the pump to a patient to deliver insulin is or is likely to become dislodged from the patient. If it is determined that the infusion set is or is likely to become dislodged from the patient, the processor can display an alert or warning on the user interface of the potential dislodgement. The processor can determine that a dislodgement or likely dislodgement is present if the readings from the glucose sensor are sufficiently high or sufficiently low relative to an expected baseline.

In some embodiments, a portable infusion system includes a portable insulin pump, a glucose sensor and an infusion set. The portable insulin pump can include a user interface, a receiver and a processor. The glucose sensor can obtain information relating to glucose levels of a patient that are received by the portable insulin pump at the receiver. The infusion set can include a cannula for insertion into the skin of the patient, tubing to deliver insulin transmitted by the pump to the cannula and an adhesive patch to retain the infusion set on the patient. The processor of the portable insulin pump can analyze information obtained by the glucose sensor to determine if the cannula is or is likely to become dislodged from the patient. An alert can be provided on the user interface of the portable insulin pump if it is determined that the cannula is or is likely to become dislodged.

In other embodiments, a portable infusion pump can deliver fluid to a patient through an infusion set including tubing extending to a cannula inserted into the patient and an adhesive patch for retaining the cannula in the patient. A sensor, such as, for example, a temperature, pressure or capacitance sensor, can be held against the patient's skin by the patch. If there is a large deviation in a subsequent sensor reading from a baseline reading it can indicate that the sensor is no longer against the patient's skin due to loosening of the patch. This loosening of the patch indicates that the cannula may have become dislodged from the patient.

Certain embodiments are described further in the following description, examples, claims, and drawings. These embodiments will become more apparent from the following detailed description when taken in conjunction with the accompanying exemplary drawings.

DETAILED DESCRIPTION

Provided herein are systems, devices and methods for detecting dislodgement of an infusion set of an infusion pump and particularly in an insulin pump. Some embodiments may include advances in the internal components, the control circuitry, and improvements in a user interface of the systems and devices. The advances may allow for a safer and more accurate delivery of medicament to a patient than is currently attainable today from other devices, systems, and methods. Although embodiments described herein may be discussed in the context of the controlled delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

Figure 1:
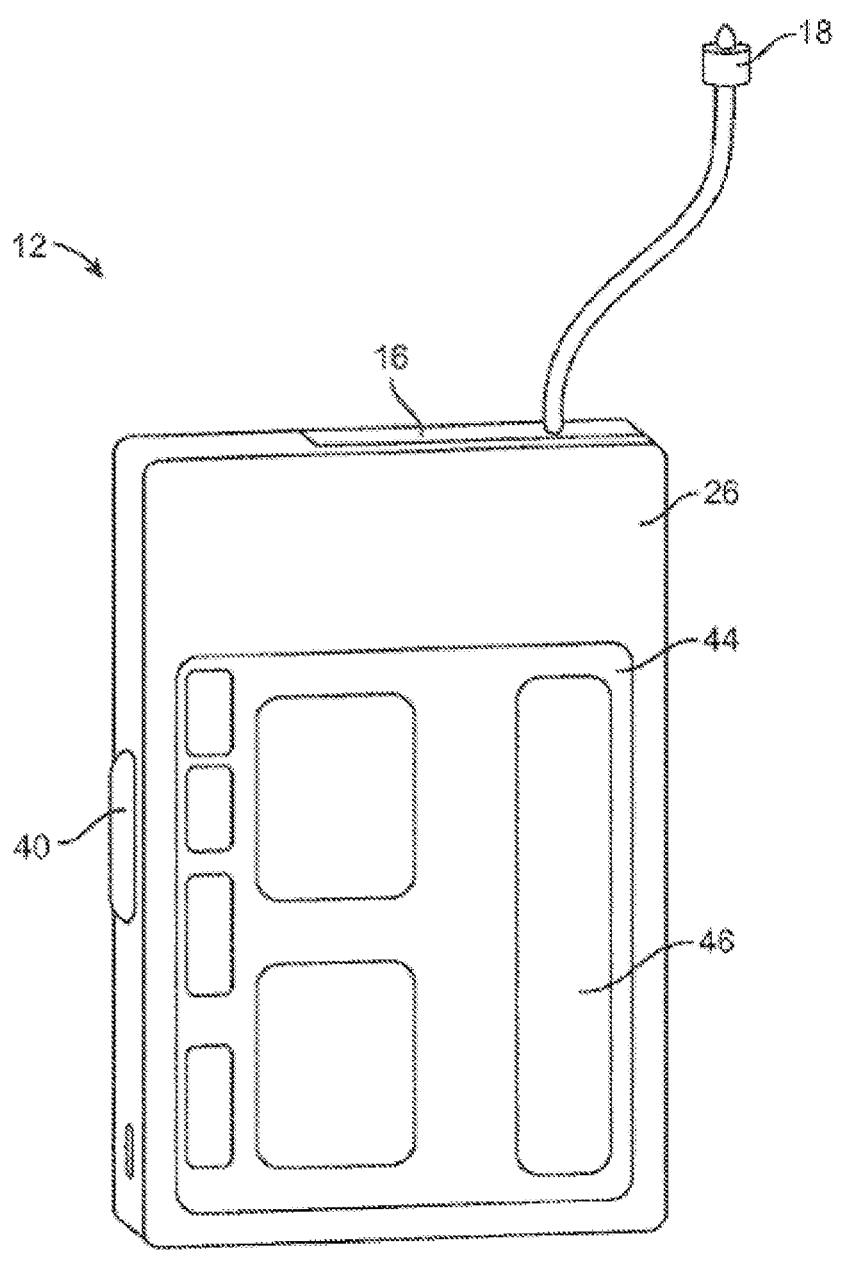
FIG. 1 is a perspective view of an infusion pump according to an embodiment of the present invention.

FIG. 1 depicts an embodiment of a pump 12 such as a portable infusion pump that can include an internal pumping or delivery mechanism and reservoir for delivering medicament such as insulin to a patient and an output/display 44. The type of output/display 44 may vary as may be useful for a particular application. The type of visual output/display may include LCD displays, LED displays, plasma displays, OLED displays and the like. The output/display 44 may also be an interactive or touch sensitive screen 46 having an input device such as, for example, a touch screen comprising a capacitive screen or a resistive screen. The pump 12 may additionally include a keyboard or other input device known in the art for data entry, which may be integrated with or separate from the display. The output/display 44 of the pump 12 may also include a capability to operatively couple to a secondary display device such as a remote display, a remote control device, a laptop computer, mobile communication device such as a smartphone or personal digital assistant (PDA) or the like. Further details regarding such pump devices can be found in U.S. Patent Application No. 2011/0144586, which is incorporated herein by reference.

Figure 2:
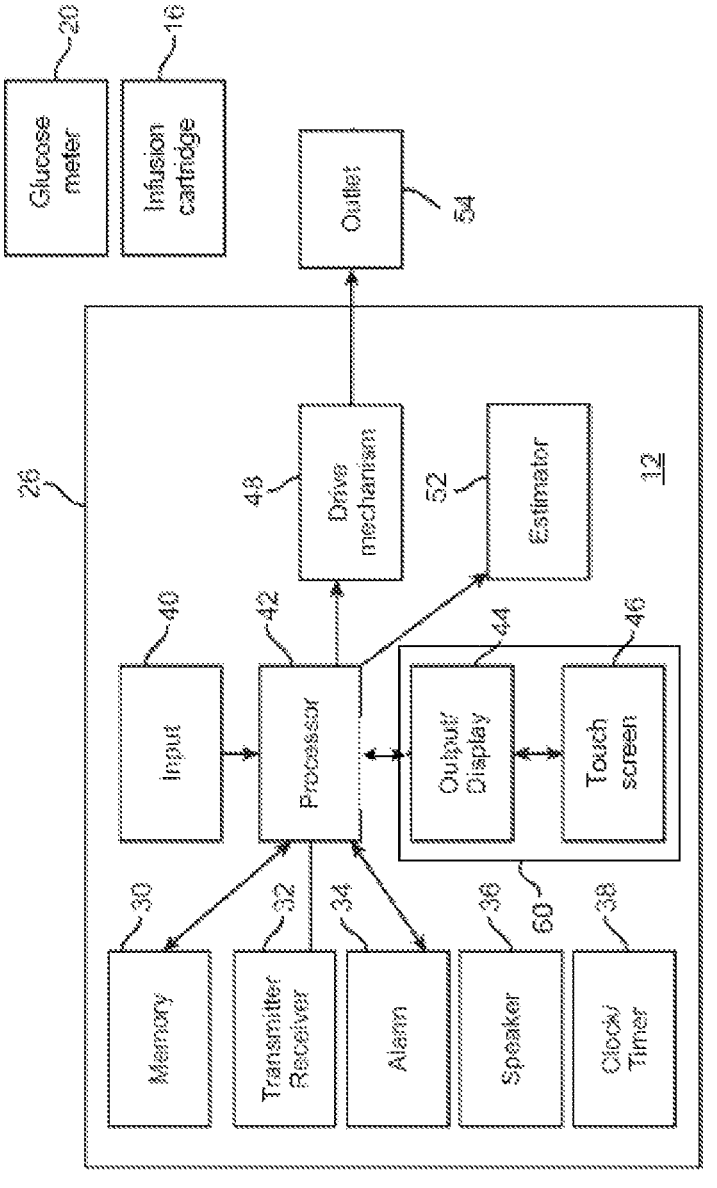
FIG. 2 is a block diagram representing an embodiment of an infusion pump.

FIG. 2 illustrates a block diagram of some of the features that may be incorporated within the housing 26 of the pump 12. The pump 12 includes a processor 42 that functions to control the overall functions of the device. The infusion pump 12 may also include a memory device 30, transmitter/receiver 32, an alarm 34, a speaker 36, a clock/timer 38, an input device 40, the processor 42, a user interface suitable for accepting input and commands from a user such as a caregiver or patient, a drive mechanism 48, and an estimator device 52. One embodiment of a user interface as shown in FIG. 2 is a graphical user interface (GUI) 60 having a touch sensitive screen 46 with input capability. The memory device 30 may be coupled to the processor 42 to receive and store input data and to communicate that data to the processor 42. The input data may include user input data and non-user/sensor input data. The input data from the memory device 30 may be used to generate therapeutic parameters for the infusion pump 12. The GUI 60 may be configured for displaying a request for the user to input data and for receiving user input data in response to the request, and communicating that data to the memory.

The processor 42 may communicate with and/or otherwise control the drive mechanism, output/display, memory, a transmitter/receiver and other components. In some embodiments, the processor 42 may communicate with another processor within the pump 12 and/or one or more processors of devices, for example, a continuous glucose monitor (CGM), display device, smartphone, etc. through the transmitter/receiver. The processor 42 may include programming that can be run to control the infusion of insulin or other medicament from the cartridge, the data to be displayed by the display, the data to be transmitted via the transmitter, etc. The processor 42 may also include programming that may allow the processor to receive signals and/or other data from an input device, such as a sensor for sensing pressure, temperature, motion/activity or other parameters. The processor 42 may determine the capacity of the drug delivery reservoir and/or the volume of fluid disposed in the drug delivery reservoir and may set therapeutic parameters based on its determination.

The processor 42 may also include additional programming to allow the processor 42 to learn user preferences and/or user characteristics and/or user history data. This information can be utilized to implement changes in use, suggestions based on detected trends, such as, weight gain or loss. The processor can also include programming that allows the device to generate reports, such as reports based upon user history, compliance, trending, and/or other such data. Additionally, infusion pump device embodiments of the disclosure may include a "power off" or "suspend" function for suspending one or more functions of the device, such as, suspending a delivery protocol, and/or for powering off the device or the delivery mechanism thereof. For some embodiments, two or more processors may be used for controller functions of the infusion pump devices, including a high power controller and a low power controller used to maintain programming and pumping functions in low power mode in order to save battery life.

The memory device 30 may be any type of memory capable of storing data and communicating that data to one or more other components of the device, such as the processor. The memory may be one or more of a Flash memory, SRAM, ROM, DRAM, RAM, EPROM and dynamic storage, for example. For instance, the memory may be coupled to the processor and configured to receive and store input data and/or store one or more templates or generated delivery patterns. For example, the memory can be configured to store one or more personalized (e.g., user defined) delivery profiles, such as a profile based on a user's selection and/or grouping of various input factors, past generated delivery profiles, recommended delivery profiles, one or more traditional delivery profiles, e.g., square wave, dual wave, basal rate and bolus profiles, and/or the like. The memory can also store, for example, user information, history of use, glucose measurements, compliance and an accessible calendar of events.

The housing 26 of the pump 12 may be functionally associated with an interchangeable and a removable glucose meter 20 and/or one or more infusion cartridges 16. The infusion cartridge 16 may have an outlet port 54 that may be connected to an infusion set via an infusion set connector 18 or to an infusion set and continuous glucose monitoring sensor combination. Further details regarding some embodiments of various infusion pump devices can be found in U.S. Patent Application No. 2011/0144586, which is hereby incorporated by reference.

Figure 3:
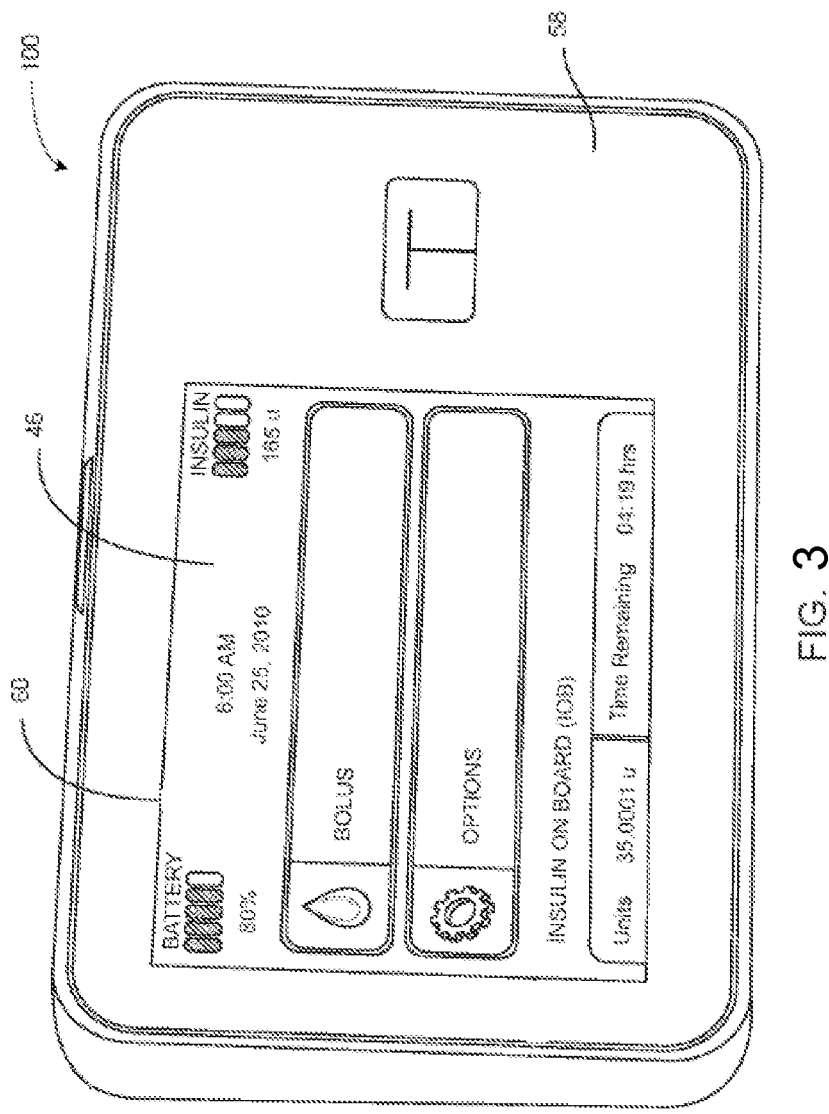
FIG. 3 depicts a screen shot of a graphical user interface of an infusion pump according to an embodiment of the present invention.

Referring to FIG. 3, a front view of an embodiment of the pump 12 is depicted. The pump 12 may include a user interface, such as, for example, a user-friendly GUI 60 on a front surface 58 or other convenient location of the pump 12. The GUI 60 may include a touch-sensitive screen 46 that may be configured for displaying data, facilitating data entry by a patient, providing visual tutorials, as well as other interface features that may be useful to the patient operating the pump 12.

Figure 4A:
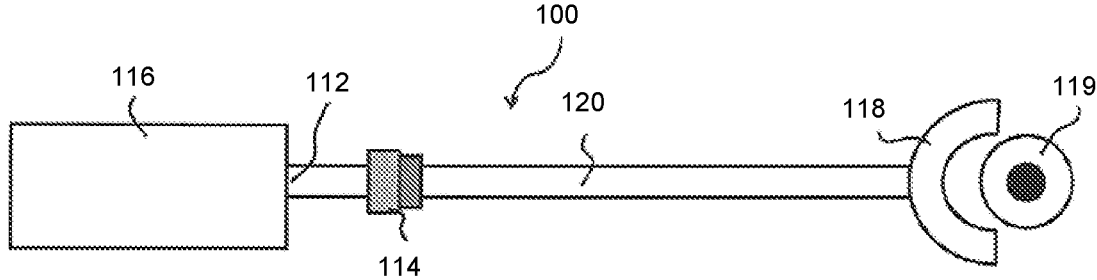
FIG. 4A depicts a schematic representation of an infusion set for use with an infusion pump according to an embodiment of the present invention.
Figure 4B:
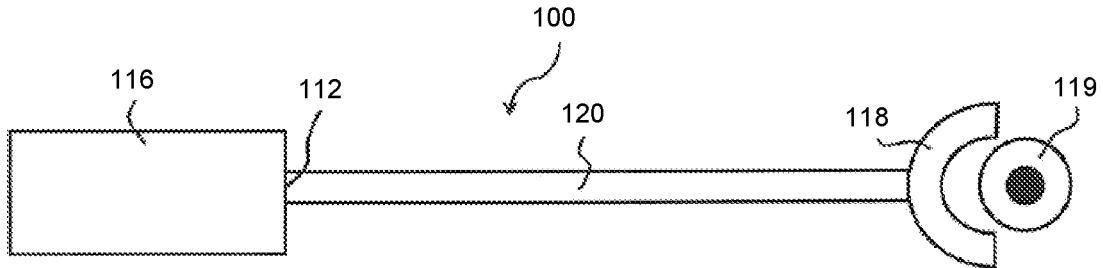
FIG. 4B depicts a schematic representation of an infusion set for use with an infusion pump according to an embodiment of the present invention.

FIGS. 4A and 4B depict embodiments of infusion sets 100 that can be used with infusion pumps as described herein to deliver medicament to a patient. Each infusion set can attach to one or more infusion cartridges, such as infusion cartridge 16 or 116. The infusion cartridge 116 can have one or more outlet ports or dispense ports 112 that can be connected to one or more infusion sets 100 at a proximal end of a length of tubing 120. The distal end of the length of tubing 120 can include a connector 118 that can attach or be pre-connected to a cannula and/or infusion needle that punctures the patient's skin at the infusion site 119. The tubing 120 is connected to the cannula with an inner lumen of the tubing 620 in fluid communication with an inner lumen of the cannula or infusion needle. In some embodiments, as shown in FIG. 4A, an infusion set connector 614 including a short length of tubing and a male lock fitting, such as a Luer lock fitting, can attach to a second length of tubing having a corresponding female lock fitting and the connector 118. In other embodiments, as shown in FIG. 4B, the infusion set 110 and corresponding tubing 120 can be preattached to the cartridge 116 such that the tubing 120 can extend from the port to the connector as a solid, uninterrupted and unitary piece of tubing with a constant diameter and having no connectors connecting portions of the tubing. Further details regarding examples of infusion sets that can be used in embodiments of the present invention can be found in U.S. patent application Ser. No. 13/827,383, which is hereby incorporated by reference.

Figure 5A:
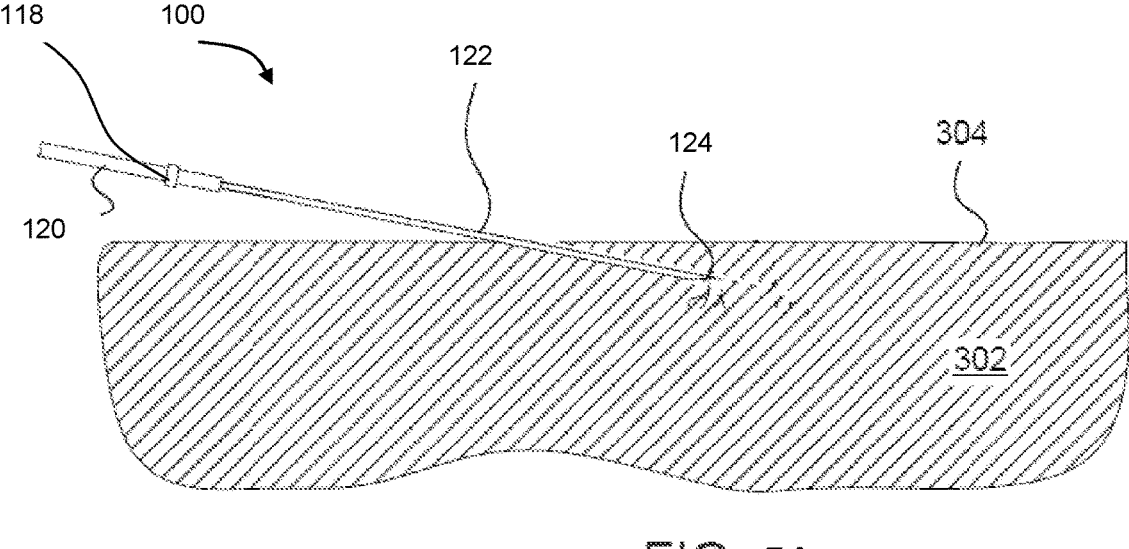
FIG. 5A depicts a schematic representation of a portion of an infusion set for use with an infusion pump according to an embodiment of the present invention inserted into a patient.
Figure 5B:
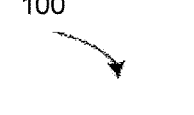
FIG. 5B depicts a schematic representation of a portion of an infusion set for use with an infusion pump according to an embodiment of the present invention inserted into a patient.
Figure 5B:
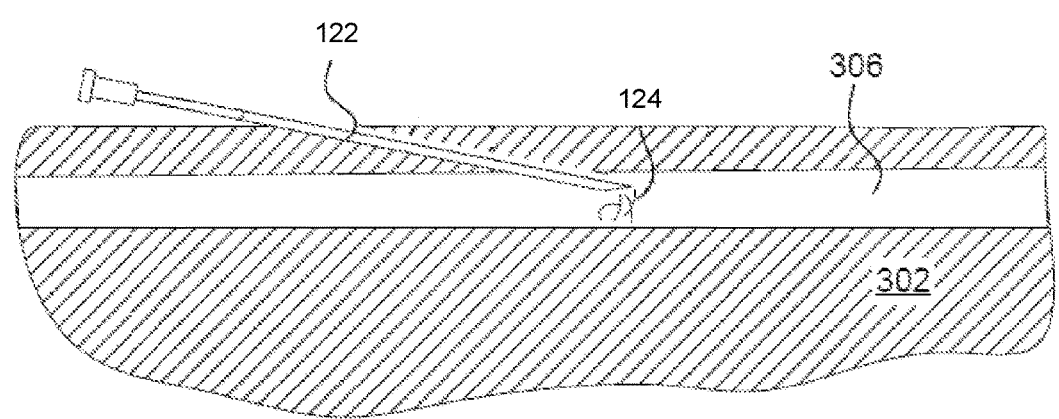

FIGS. 5A-5B depict an infusion set 100 with a cannula 122 at distal ends of fluid tubing 120 of the infusion set 100 inserted into a patient's body 302. The cannula 122 can be inserted in a subcutaneous space under the patient's skin 304 as shown in FIG. 5A. Alternatively, the cannula 122 can be disposed within an inner lumen of a patient's fluid vessel 306, such as shown in FIG. 5B. The infusion set 100 is in fluid communication with a dispense port of an infusion pump system, and fluids such as insulin and/or other suitable medicaments are shown being dispensed from an outlet port 124 of the cannula 122 and into the patient's body 302. The distal ends of the fluid tubing may be held in place by a piece of an adhesive pad (not shown in FIGS. 5A-5B) secured to the patient's skin 304.

Figure 6A:
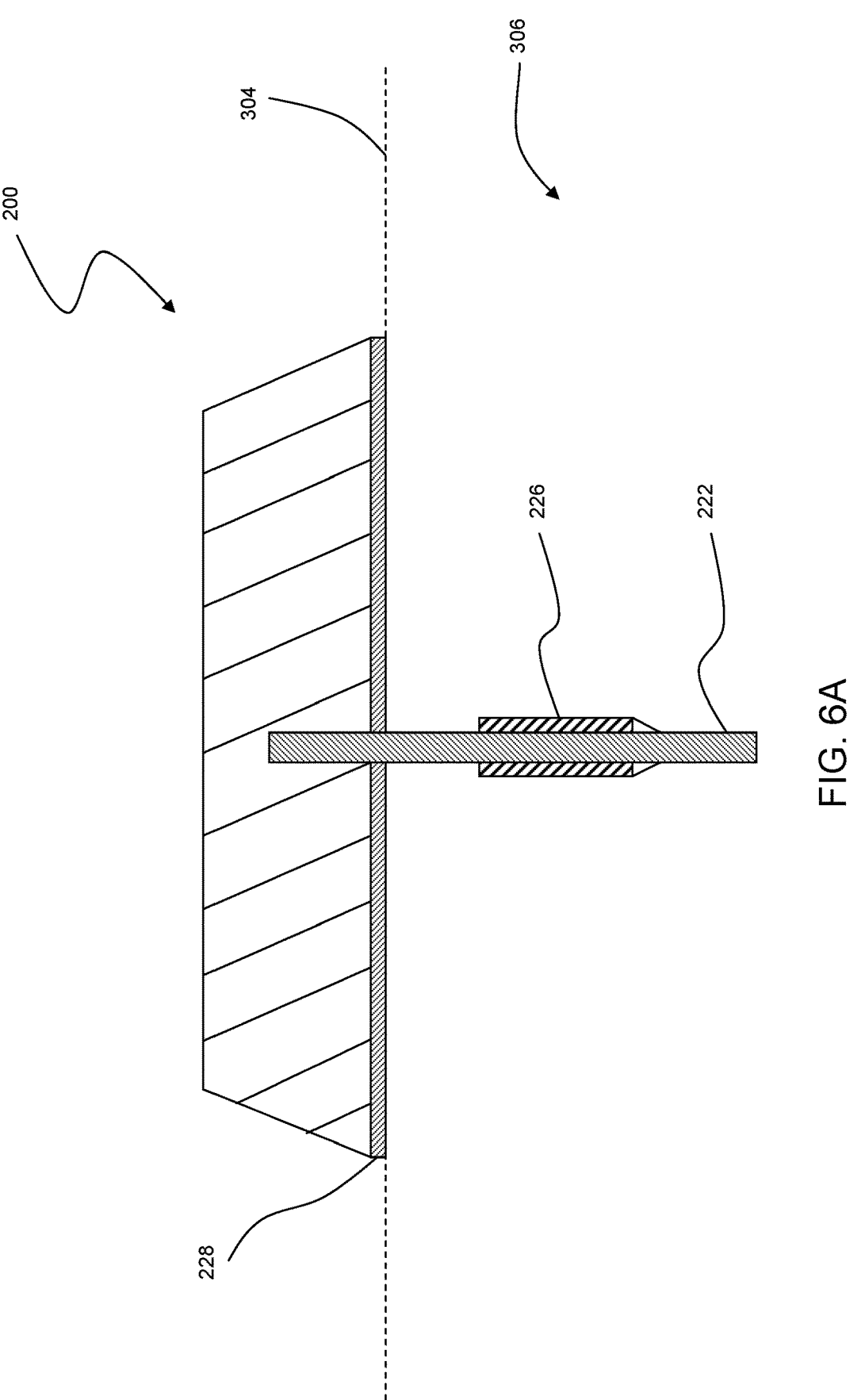
FIG. 6A depicts a schematic cross-sectional representation of a portion of an infusion set for use with an infusion pump according to an embodiment of the present invention.

Referring now to FIG. 6A, a schematic representation of a portion of an embodiment of the present invention depicts an infusion set 200 including an integrated glucose sensor 226. The sensor 226 can be part of a continuous glucose monitoring system (CGM) that provides a substantially continuous estimated glucose level via, e.g., a transcutaneous sensor 226 that measures analytes in the patient's interstitial fluid to estimate, e.g., blood glucose levels. The sensor 226 reacts with the interstitial fluid to produce a signal that can be calibrated with the patient's blood glucose (BG) level. The data may be transmitted from the sensor 226 to the glucose monitoring system via a wireless transmitter, such as a near field communication (NFC) radio frequency (RF) transmitter or a transmitter operating according to a "WiFi" or "Bluetooth" protocol or the like, or the data may be transmitted via a wire connector from the sensor 226 to the monitor system. Alternatively, the sensor 226 can transmit the data directly to the infusion pump 12. Further detail regarding such CGM systems and definitions of related terms can be found in, e.g., U.S. Pat. Nos. 8,311,749, 7,711,402 and 7,497,827 and in U.S. patent application Ser. No. 13/800,453, each of which is hereby incorporated by reference in its entirety.

As shown in FIG. 6A, the infusion set 200 can be affixed to the patient's skin 304 with an adhesive patch or layer 228. Adhesive layer 228 can comprise a flexible material such as a polymer with an adhesive coating. The cannula 222, which receives fluid from the pump through tubing, extends through the adhesive layer 228 and into the patient's body 302 for delivery of the fluid. In the embodiment depicted in FIG. 6A, the CGM sensor 226 is integrated around the cannula 222 such that the sensor and cannula share a single site. As the cannula 222 is utilized to deliver fluid to the patient, the CGM sensor transmits readings back to the CGM monitor and/or the pump that are indicative of the patient's glucose level, as described above. Although depicted in FIG. 6A as being disposed around the cannula 222, the CGM sensor 226 could be integrated in a number of additional ways, such as being disposed within the cannula 222. Alternatively, as shown in FIG. 6B, the sensor 126 can be inserted at a separate insertion site from the cannula 222 but mechanically linked to the cannula 222 by, for example, also extending from the adhesive backing 228 connecting the infusion set 200 to the patient's skin 304.

Figure 6B:
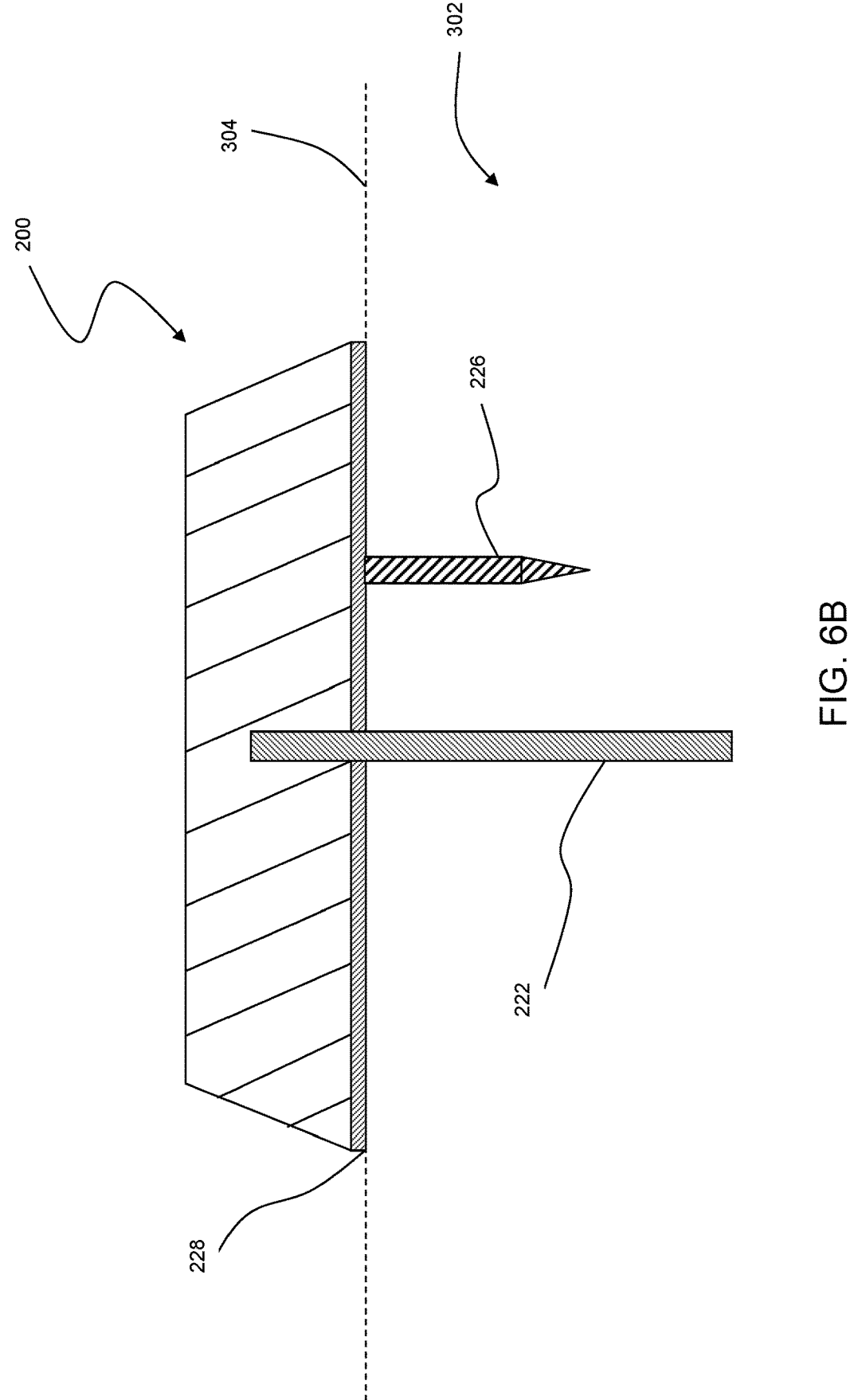
FIG. 6B depicts a schematic cross-sectional representation of a portion of an infusion set for use with an infusion pump according to an embodiment of the present invention.

A system that integrates a glucose sensor 226 such as a CGM sensor with a delivery cannula 222 such as shown in FIGS. 6A and 6B, for example, can be utilized to determine if the delivery cannula 222 has accidentally become dislodged from the patient's body 302. As noted above, the sensor obtains readings of analyte levels in the patient's interstitial fluid that can be correlated to the patient's blood glucose levels. While the cannula 222 and sensor 226 are in the patient's body, the CGM will provide readings in an expected or acceptable range relating to typical glucose levels of a patient (whether, e.g., normal, low or high). However, if the CGM sensor 226 becomes dislodged and physically separated from the patient's body and is in contact with, e.g., the ambient air or the patient's clothing rather than the patient's interstitial fluid, the readings may be sufficiently high or low to be outside of the expected range. Such readings, which can be moderately or even severely out of the expected range, may therefore be indicative of dislodgement of the CGM sensor from the skin. In embodiments such as that depicted in FIG. 6A, the disconnection of the CGM sensor 226 directly indicates that the cannula 222 is also dislodged from the skin. In embodiments where the CGM sensor 226 and the cannula 222 are inserted separately, such as in FIG. 6B, such measurements may indicate that the cannula 222 is either likely also dislodged or is likely to become dislodged, because if the adhesive backing 228 or other mechanical connection has pulled out the sensor 226 it likely either has or will also pull out the cannula 222.

Figure 7A:
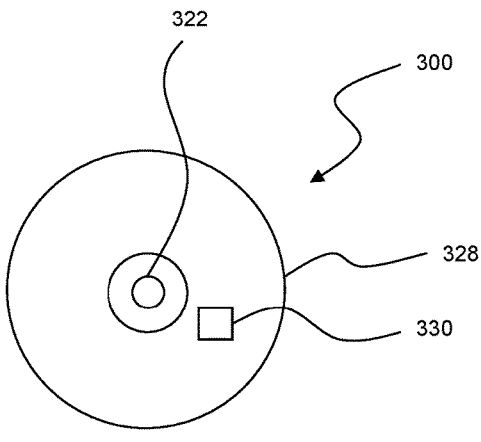
FIG. 7A depicts a schematic representation of a portion of an infusion set for use with an infusion pump according to an embodiment of the present invention.
Figure 7B:
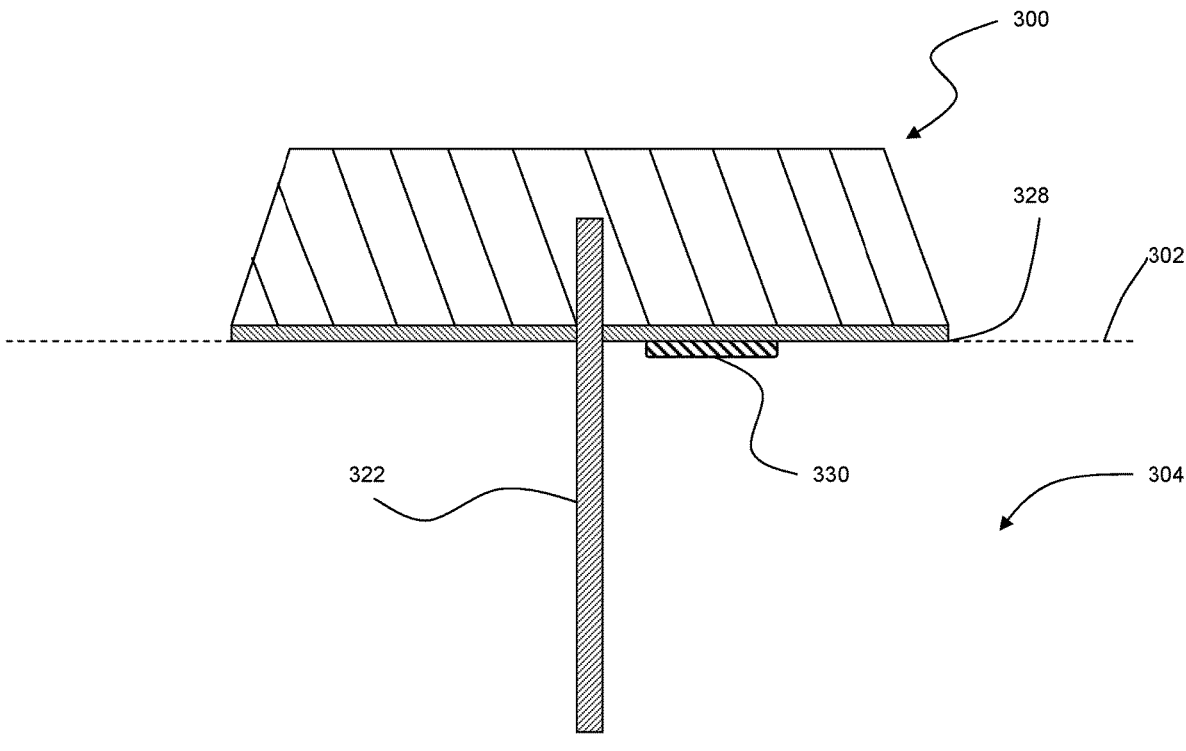
FIG. 7B depicts a schematic cross-sectional representation of a portion of an infusion set for use with an infusion pump according to an embodiment of the present invention.
Figure 8:
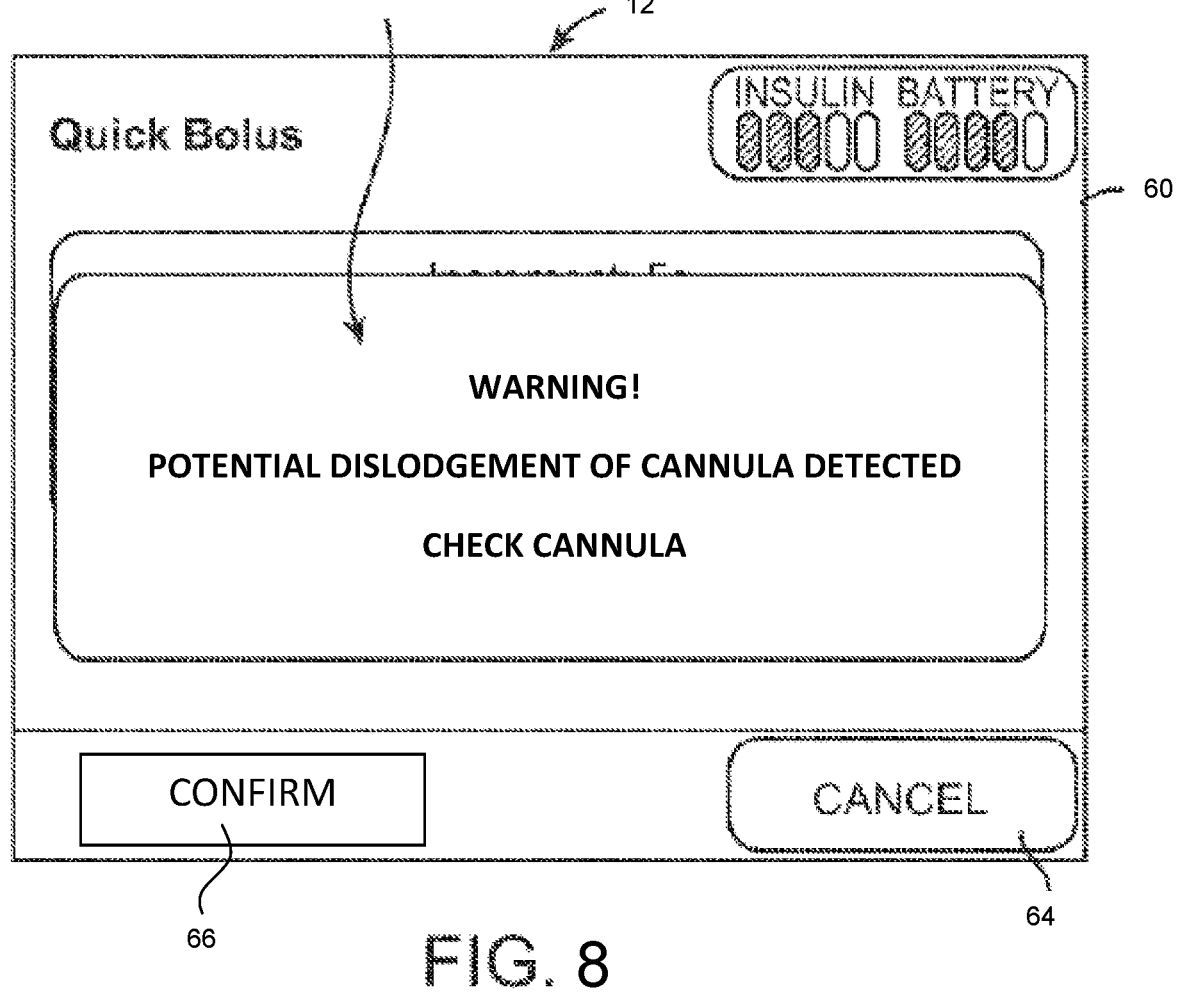
FIG. 8 depicts a screen shot of a user interface of an infusion pump according to an embodiment of the present invention.

FIGS. 7A and 7B depict a portion of another embodiment of an infusion set 300 that can be utilized to determine if the cannula 322 has become dislodged from the skin. A sensor 330 can be affixed to the adhesive coating of the adhesive layer such that it is disposed directly against the patient's skin when the adhesive layer 328 is properly attached to the skin. In certain embodiments, the sensor 330 can be, for example, a temperature sensor, a pressure sensor or a capacitance sensor. The sensor 330 can also be a sensor for measuring an ECG or other such physiological parameter. When the adhesive layer 328 of the infusion set 300 is properly attached to the skin 302, the sensor 330 will be in constant contact with the skin. Thus, the temperature, pressure, capacitance, ECG, etc. readings will remain nominal, e.g., relatively constant. If the sensor 330 deviates from this generally constant level in a relatively short period of time or otherwise indicates an abnormal or unexpected reading, it can indicate that the sensor 330 is no longer in contact with the patient's skin. If the adhesive backing 128 has peeled away such that the sensor 330 is no longer in contact with the patient's skin, it is an indication that the cannula 322 has become or is likely to become dislodged from the body 304 of the patient. Although depicted as being attached to the adhesive layer 328, sensor 330 can be attached to any portion of infusion set 300 that puts it into contact with the patient, such as, for example, on an outer surface of the cannula 322.

If the CGM readings of any of the systems described above indicate that the cannula of an infusion set may have come dislodged from the patient, a user interface 60 of the corresponding infusion pump 12 system can provide a warning 62 indicating that the cannula may have dislodged and prompting the user to check the cannula for dislodgement. The user can then have the option of selecting a confirm object 66 to confirm the cannula is properly inserted or cancelling the warning with a cancel object 64. In some embodiments, the pump can automatically stop delivering fluid until the user has indicated that the cannula is properly attached. In certain embodiments, the pump 12 can obtain the CGM readings, via the receiver 32, either directly from the CGM sensor or from a standalone CGM monitor via a wires or wired connection. A similar notification screen could be provided for any of the embodiments described with reference to FIGS. 7A and 7B in which other sensed parameters indicate a likely dislodgement. In certain embodiments, such a warning is provided if a sensor reading deviates from a baseline level by a threshold amount or otherwise crosses a low and/or high threshold for a particular type of sensor.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

Also incorporated herein by reference in their entirety are commonly owned U.S. Pat. Nos. 8,287,495; 8,408,421 and 8,448,824; commonly owned U.S. Patent Publication Nos. 2009/0287180; 2010/0008795; 2010/0071446; 2010/0218586; 2012/0123230 and 2013/0053816; and commonly owned U.S. patent application Ser. Nos. 13/800,387; 13/800,453; 13/800,595; 13/801,230; 13/801,274; 13/827,383; 13/827,707; 13/828,958; 13/829,115; 13/832,531; 13/832,841; 13/837,661; 13/837,777; 13/838,084; 13/841,432; 13/842,005 and 13/842,990.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or dates of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. A method of providing diabetes therapy to a patient with a portable infusion pump, comprising:

delivering medicament to a patient with the portable infusion pump through a cannula inserted into the patient;

monitoring glucose levels of the patent with data obtained by a glucose sensor while the medicament is delivered to the patient;

determining that the monitored glucose levels are inconsistent with expected readings;

determining, due to the monitored glucose levels being inconsistent with expected readings, that the patient may not be receiving the medicament through the cannula; and providing an alert to the patient to check the portable infusion pump in response to the determination that the patient may not be receiving the medicament through the cannula.

2. The method of claim 1, wherein determining that the monitored glucose levels are inconsistent with expected readings includes determining that the glucose levels are higher than expected.

3. The method of claim 1, wherein providing an alert to the patient to check the portable infusion pump includes providing a textual alert instructing the user to check the portable infusion pump.

4. The method of claim 1, wherein providing an alert to the patient to check the portable infusion pump includes providing a visual alert on a display of the portable infusion pump.

5. The method of claim 1, wherein providing an alert to the patient to check the portable infusion pump includes providing the alert on a display of a remote control device for the portable infusion pump.

6. The method of claim 1, further comprising providing a selectable icon for the patient to respond to the alert.

7. The method of claim 1, further comprising discontinuing delivery of medicament with the portable infusion pump upon determining that the patient may not be receiving the medicament through the cannula.

8. A method of providing diabetes therapy to a patient with a portable infusion pump, comprising:

delivering medicament to a patient with the portable infusion pump through a cannula inserted into the patient;

monitoring glucose levels of the patent with data obtained by a glucose sensor while the medicament is delivered to the patient;

determining that the monitored glucose levels are not responding to delivery of the medicament as expected; and providing an alert to the patient to check the portable infusion pump in response to the determination that the monitored glucose levels are not responding to delivery of the medicament as expected.

9. The method of claim 8, wherein determining that the monitored glucose levels are not responding to delivery of the medicament as expected includes determining that the glucose levels are higher than expected.

10. The method of claim 8, wherein providing an alert to the patient to check the portable infusion pump includes providing a textual alert instructing the user to check the portable infusion pump.

11. The method of claim 8, wherein providing an alert to the patient to check the portable infusion pump includes providing the alert on a display of the portable infusion pump.

12. The method of claim 8, wherein providing an alert to the patient to check the portable infusion pump includes providing the alert on a display of a remote control device for the portable infusion pump.

13. The method of claim 8, further comprising providing a selectable icon for the patient to respond to the alert.

14. The method of claim 8, further comprising discontinuing delivery of medicament with the portable infusion pump upon determining that the monitored glucose levels are not responding to delivery of the medicament as expected.

15. A portable infusion pump system, comprising:

a portable infusion pump including a reservoir configured to contain a medicament and a delivery mechanism configured to deliver the medicament to a patient through a cannula inserted into the patient;

a receiver adapted to receive data relating to glucose levels of the patient obtained by a glucose sensor; and a processor configured to:

cause the delivery mechanism to deliver the medicament to the patient through the cannula;

monitor glucose levels of the patent with the data obtained by the glucose sensor while the medicament is delivered to the patient;

determine that the monitored glucose levels are inconsistent with expected readings;

determine, due to the monitored glucose levels being inconsistent with expected readings, that the patient may not be receiving the medicament through the cannula; and provide an alert to the patient to check the portable infusion pump in response to the determination that the patient may not be receiving the medicament through the cannula.

16. The system of claim 15, wherein the processor is configured to determine that the monitored glucose levels are inconsistent with expected readings by determining that the glucose levels are higher than expected.

17. The system of claim 15, wherein the processor is configured to provide the alert to the patient by providing a textual alert instructing the user to check the portable infusion pump.

18. The system of claim 15, wherein the alert is provided by the portable infusion pump.

19. The system of claim 15, wherein the alert is provided by a remote control device for remotely controlling the portable infusion.

20. The system of claim 15, wherein the processor is further configured to display a selectable icon for the patient to respond to the alert.

\* \* \* \* \*